(12) United States Patent
Marfurt

(10) Patent No.: US 7,439,033 B2
(45) Date of Patent: Oct. 21, 2008

(54) METHOD AND TEST STRIP FOR DETERMINING A FLUID ANALYTE

(75) Inventor: Karen L. Marfurt, Mishawaka, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 707 days.

(21) Appl. No.: 10/767,963

(22) Filed: Jan. 29, 2004

(65) Prior Publication Data
US 2004/0185517 A1    Sep. 23, 2004

Related U.S. Application Data

(60) Provisional application No. 60/444,414, filed on Feb. 4, 2003.

(51) Int. Cl.
*C12Q 1/54* (2006.01)

(52) U.S. Cl. .............................. 435/14; 435/4; 436/169; 436/95; 422/56

(58) Field of Classification Search .......... 435/4–40.52; 436/95, 164–172; 422/56–58
See application file for complete search history.

(56) References Cited

U.S. PATENT DOCUMENTS

| | | | |
|---|---|---|---|
| 4,935,346 A | 6/1990 | Phillips et al. ................. 435/14 |
| 5,049,394 A | 9/1991 | Howard et al. ............... 424/490 |
| 5,049,487 A | 9/1991 | Phillips et al. .................. 435/4 |
| 5,126,275 A | 6/1992 | Hatch et al. .................. 436/169 |
| 5,179,005 A | 1/1993 | Phillips et al. ................. 435/14 |
| 5,304,468 A | 4/1994 | Phillips et al. ................. 435/14 |
| 5,306,623 A * | 4/1994 | Kiser et al. .................... 435/14 |
| 5,322,680 A | 6/1994 | Beck et al. ..................... 428/71 |
| 5,360,595 A * | 11/1994 | Bell et al. ...................... 422/56 |
| 5,462,866 A * | 10/1995 | Wang ......................... 435/174 |
| 5,484,708 A | 1/1996 | Hoenes et al. ................ 435/14 |
| 5,520,786 A | 5/1996 | Bloczynski et al. .......... 204/403 |
| 5,789,255 A | 8/1998 | Yu ................................ 536/95 |
| 5,968,765 A * | 10/1999 | Grage et al. ................... 435/25 |
| 5,972,294 A * | 10/1999 | Smith et al. ................... 422/58 |
| 6,040,195 A * | 3/2000 | Carroll et al. ................ 436/514 |
| 6,162,397 A * | 12/2000 | Jurik et al. .................... 422/56 |
| 6,284,194 B1 * | 9/2001 | Chu ............................. 422/55 |
| 6,696,240 B1 * | 2/2004 | Kloepfer et al. ................ 435/4 |
| 2003/0106809 A1 * | 6/2003 | Kermani et al. ............. 205/775 |
| 2003/0175153 A1 * | 9/2003 | Anaokar et al. ............... 422/56 |
| 2004/0185517 A1 | 9/2004 | Marfurt ....................... 435/14 |

FOREIGN PATENT DOCUMENTS

| | | |
|---|---|---|
| CN | 1169533 A | 1/1998 |
| CN | 1231212 A | 10/1999 |
| EP | 0 475 692 A1 | 3/1992 |
| EP | 0 476 454 B1 | 10/1996 |
| EP | 0 747 984 A2 | 12/1996 |
| EP | 0 985 930 A2 | 3/2000 |
| EP | 1 167 519 A1 | 1/2002 |

* cited by examiner

*Primary Examiner*—Jill Warden
*Assistant Examiner*—Imran Akram
(74) *Attorney, Agent, or Firm*—Nixon Peabody, LLP

(57) ABSTRACT

A reagent strip for measuring the concentration of glucose in whole blood has a polymer on at least one side thereof to increase the opacity thereof, thereby reducing the effect of hematocrit on the glucose determination.

22 Claims, 5 Drawing Sheets

METHOD AND TEST STRIP FOR DETERMINING A FLUID ANALYTE

CROSS-REFERENCE TO RELATED APPLICATION

This application claims priority to Application No. 60/444,414 filed on Feb. 4, 2003.

The instant invention relates to a method and test strips for determining the amount of an analyte within a sample. More particularly, this invention relates to a method for determining the amount of glucose in blood, and to sample strips useful in such a method.

BACKGROUND OF THE INVENTION

It has become increasingly important to medical science to be able to quantify the chemical and biochemical components of a wide variety of fluids, particularly colored aqueous biological fluids such as whole blood and urine, and biological derivatives such as serum and plasma. Such ability is important in testing for exposure to hazardous materials, intoxicants, and therapeutic drugs, and in diagnostics. In some applications, it is important for a lay person to be able to perform the test outside a laboratory environment, with rapid and accurate results. For example, diabetics must test samples of their own blood for glucose several times a day to moderate their diet and medication. The test results must be both rapidly available and accurate.

Test kits for the determination of glucose in blood are well known in the art. Such test kits often involve a test strip impregnated with one or more chemicals that react in the presence of glucose to cause a color change in the test strip. The color change in the test strip is measured by known optical detection methods. While a change in either absorption, transmittance, or reflectance of a sample can be measured, typically for glucose determinations the change in reflectance is measured. Generally, as the glucose concentration in a sample increases, the strip will generate more color and become darker. A darker test strip will give off less reflectance, such that a lower reflectance level will indicate more glucose in the sample.

The presence of red blood cells in a blood sample can interfere with the reflectance reading by reflecting light back to the detector at the same wavelength as the glucose reading is made, or by blocking the transmission of light so that all the color developed in response to glucose cannot be read, or by scattering the light. Thus some test kits require that the red blood cells be filtered out of the sample or lysed prior to applying the sample to a test strip.

One series of patents relating to the colorimetric determination of glucose in blood includes U.S. Pat. Nos. 4,935,346, 5,049,487, 5,049,394, 5,179,005, and 5,304,468, all assigned to Lifescan, Inc. of Mountain View, Calif., and all incorporated herein by reference in their entireties. The method disclosed therein involves taking a reflectance reading from one surface of an inert two-sided porous matrix. The matrix is impregnated with a reagent that will interact with the analyte to produce a light-absorbing reaction product when the fluid being analyzed is applied to the first surface and migrates through the matrix to the second surface. Reflectance measurements of the second surface are made at two separate wavelengths in order to compensate for interference from hematocrit variation, and for variation caused by the chromatography of the color generated in response to glucose at a given concentration. A timing circuit is triggered by an initial decrease in reflectance caused by the wetting of the second surface by the fluid which passes through the inert matrix. The method does not require the separation of red blood cells from serum or plasma.

U.S. Pat. No. 5,484,708 assigned to Boehringer Mannheim GmbH, entitled "Method for the Colorimetric Determination of an Analyte with a PQQ-Dependent Dehydrogenase" discloses a method for the colorimetric determination of an analyte by means of enzymatic oxidation with a PQQ-dependent dehydrogenase in the presence of an electron acceptor from the group of the electron-rich aromatic nitroso compounds by enzymatic reduction of the nitroso compound to an imino compound and detection of the imino compound by color formation.

U.S. Pat. No. 5,789,255, also assigned to Lifescan, Inc. and incorporated herein by reference in its entirety, is entitled "Blood Glucose Strip having Reduced Sensitivity to Hematocrit." This patent discloses a reagent strip comprising an anisotropic membrane having a sample side with relatively large pores and a testing side with relatively small pores. A test sample is applied to the sample side and passes through the membrane toward the testing side, while the relatively large red blood cells are filtered out of the blood sample. The membrane is impregnated with a testing agent comprising a component that reacts with glucose and oxygen to create hydrogen peroxide, a color indicator that reacts with the hydrogen peroxide, and an acrylic acid-polymer that reduces the effect of the red blood cells on the glucose concentration measurement. It is believed that the acrylic acid polymers used are of relatively high molecular weight, and affect the viscosity and flow of the sample.

In such prior art methods of testing for glucose using optical detection methods, it is recognized that the detection system must adjust for the opacity of a reflective surface. It is known that a reaction surface that is more opaque will be less sensitive to the presence of red blood cells. In some such methods, the opacity is adjusted by the use of scattering centers incorporated into the reflective surface of the matrix. Such known scattering centers include titanium dioxide, diatomaceous earth, powdered metals, minerals, and various combinations of these and other materials. Other factors known to affect opacity include pore size, pore structure, and the surface area of the supporting media.

It is one object of the invention to provide a method for testing a sample of a fluid that does not require the separation or lysing of red blood cells from a whole blood sample.

It is a further object of the invention to provide such a method that can be done with a very small sample of fluid, typically less than one microliter.

It is still another object of the invention to provide such a test method that is not sensitive to variations of hematocrit from sample to sample.

It is yet another object of the invention to provide a test strip suitable for use with the inventive method.

SUMMARY OF THE INVENTION

The foregoing objects are met by the invention herein, wherein a method of determining glucose in a sample includes the use of a two-sided test strip in which one or more polymers are used to change the opacity of the surface being optically read. In a preferred embodiment, the polymer also will control the chromatography of the reaction product by maintaining the testing reagents at the reaction site and/or the read site. In accordance with the invention, a method for determining glucose concentration in a sample of whole blood comprises (a) providing a test strip having a sample side and a reaction side, the test strip being adapted to accept the sample on the sample side and pass it toward the reaction side, said test strip supporting a testing reagent, said testing reagent comprising a color indicator system that changes color to indicate the presence of glucose in the sample, said test strip further having a polymer, applied thereto at least on the reaction side, said polymer increasing the opacity of the reaction side of the test strip; (b) applying the blood sample to the sample side of the test strip; and, (c) measuring the change in color of the reaction side to determine the glucose concentration in the blood.

The test strip preferably comprises a porous membrane made from a material selected from the group consisting of polyethersulfone and modified polyethersulfones. The one or more polymers applied to the porous membrane are preferably selected from the group consisting of acrylic latex polymers and polystyrene sodium sulfate.

BRIEF DESCRIPTION OF THE FIGURES

The instant invention will be more readily understood by reference to the figures, wherein.

DETAILED DESCRIPTION OF THE INVENTION

The method of the instant invention comprises the determination of glucose in a sample by the known steps of placing the sample on a first side of a test strip, allowing any glucose in the sample to react with reagents impregnated in the test strip, and taking an optical measurement of the opposite side of the test strip after the sample has passed through the test strip. In accordance with the invention, the test strip is provided with one or more polymers that alter the opacity of the test strip in a manner that makes the glucose determination less sensitive to the presence of red blood cells in the sample. In each of FIGS. 1A-C, the thickness of the layers is shown for clarity of illustration and is not intended to be representative of the actual thicknesses of the layers in a test strip product.

Figure 1A:
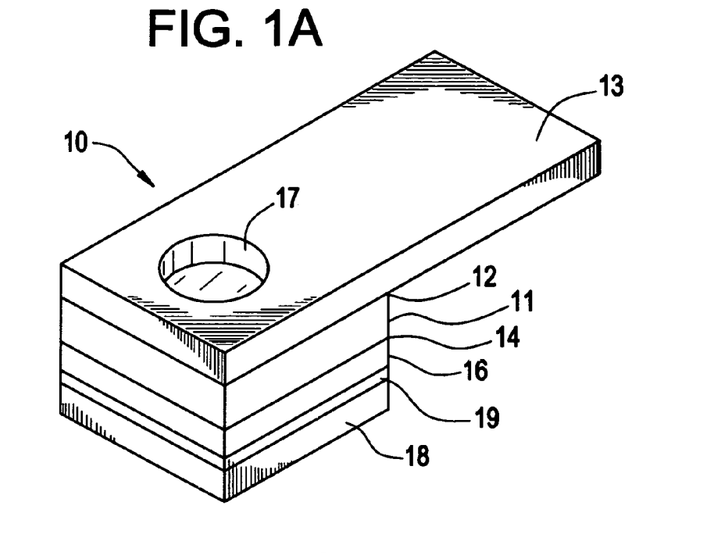
FIG. 1A is a perspective drawing of a test strip made in accordance with the instant invention.

FIG. 1A is a perspective view of a test strip 10 suitable for use in the method of the instant invention. As illustrated in the FIG. 1A, test strip 10 comprises a handle 13 to which is bonded a porous membrane 11. Because the method of the instant invention does not require filtration of red blood cells from the sample prior to making the optical measurement, the pore structure can be constant in the x, y, and z directions in the test strip, although membranes having an anisotropic pore size gradient also can be used. The porous membrane 11 has a first side 12, also known as the test side or the sample side, and a second side 14, also known as the reaction side. A sample is deposited through hole 17 in handle 13 onto test side 12 of porous membrane 11. The sample passes through the pores of the membrane to reaction side 14 of the porous membrane 11. An optical measurement of reaction side 14, such as reflectance, is then correlated with glucose concentration to determine the amount of glucose present in the sample.

In accordance with the invention, reaction side 14 of porous membrane 11 is treated with a testing reagent composition 16 comprising a color indicator system that changes color to indicate the presence of glucose in the sample, the reagent composition 16 further comprising a polymer that affects the opacity of reaction side 14 of porous membrane 11. The reagent composition 16 including the polymer can be applied to the test strip by methods such as dipping, coating, and striping. In the embodiment illustrated in FIG. 1A, the composition is applied as coating 16 over reaction side 14 of test strip 10. In another embodiment, the composition will be first applied to side 12 such as by dipping and allowed to pass through the strip to reconstitute on side 14. Those skilled in the art will be able to optimize the parameters of the composition application processes to achieve the desired composition layer 16, including the polymer. The polymer in the reagent composition can also affect the chromatography of the analyte through the test strip. An optically clear window 18 can be applied to composition 16 by known methods, including laminating or use of a pressure-sensitive adhesive 19. Window 18 can be made of polyester or any other optically suitable material.

Figure 1B:
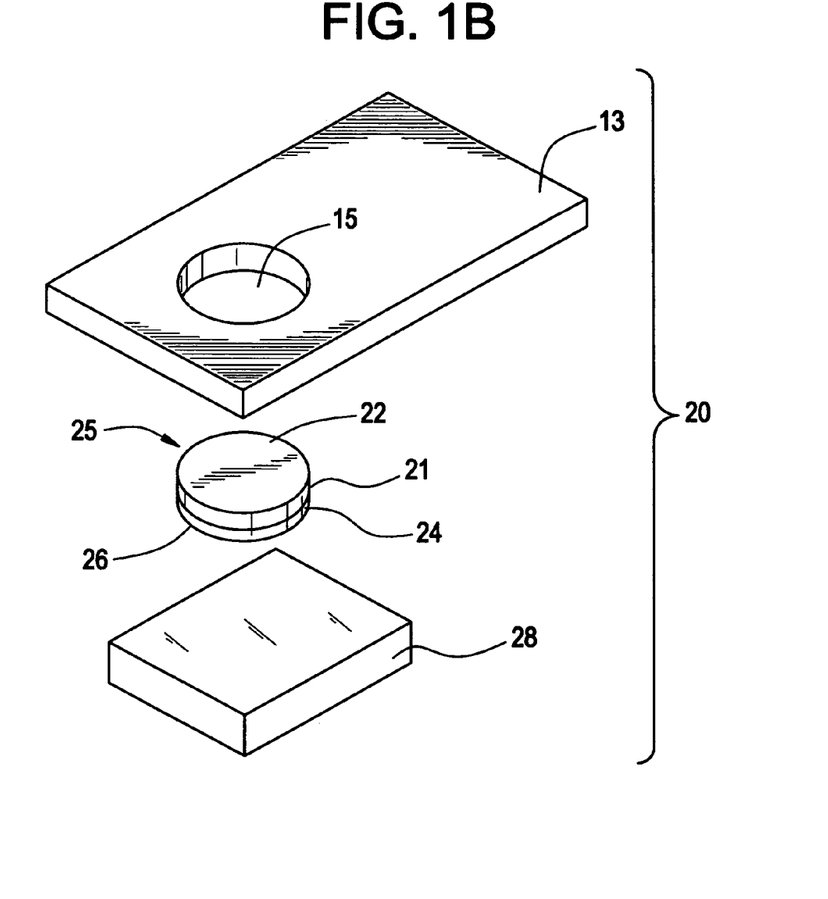
FIG. 1B is an exploded view of an alternative embodiment of a test strip made in accordance with the invention.

FIG. 1B illustrates an alternative embodiment of a test strip made in accordance with the invention. In this embodiment, test strip 20 comprises handle 13 from which has been cut a hole 15. Disc 25 comprises porous membrane 21 having a sample side 22 and a reaction side 24. Applied to reaction side 24 is a testing reagent composition 26 comprising a color indicator system that changes color to indicate the presence of glucose in the sample, and a polymer that changes the opacity of the reaction side 24 of porous membrane 21. Disc 25 is fitted into hole 15, and an optically clear window 28 is applied over disc 25 and the portion of handle 13 in which it is received. It may be seen that this embodiment requires less of the treated porous membrane material than the embodiment of FIG. 1A, or the prior art devices shown and described in the aforementioned prior art patents such as U.S. Pat. No. 5,789, 255. It will be appreciated that disc 25 can be in the form of ribbons or other suitable geometric configurations.

Figure 1C:
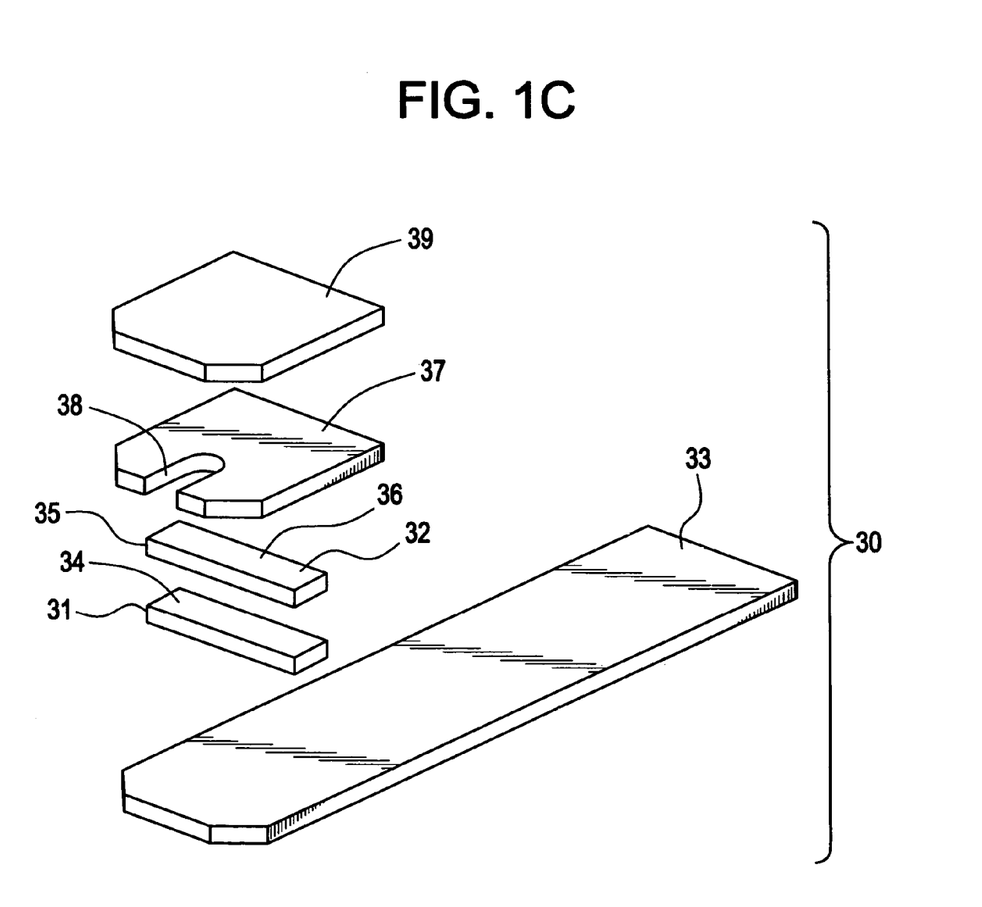
FIG. 1C is an exploded view of another alternative embodiment of a test strip suitable for use with the instant invention.

FIG. 1C illustrates yet another alternative embodiment of a test strip suitable for use with the instant invention. In this embodiment, test strip 30 comprises handle 33. Ribbon 35 comprises porous membrane 31 having a sample side 32 and a reaction side 34. The porous membrane 31 is provided on reaction side 34 with a composition 36 comprising a testing reagent comprising a color indicator system that changes color to indicate the presence of glucose in the sample and a polymer that changes the opacity of the reaction side 34 of porous membrane 31. A spacer 37 having a capillary inlet 38 is applied over a portion of strip 33 and ribbon 35 with adhesive, such that capillary inlet 38 is disposed over a portion of ribbon 35. A lid is optionally disposed over spacer 37 to protect the instrument from contamination. A window is disposed on the opposite side of the test strip.

In each of the embodiments illustrated, the porous membrane supports a reagent composition that reacts in the presence of glucose to produce a reaction product that can be measured with an optical detector to allow quantitative determination of glucose. The chemistry of the reaction can be either reductive or oxidative. A reductive chemistry system suitable for use with the instant invention can be, for example, either a PQQ-GDH or a NAD-dependent GDH system. A hexokinase reductive system also can be used, as can a glucose oxidase oxidative system. For the NAD dependent GDH system, appropriate mediators include, without limitation, those disclosed in U.S. Pat. No. 5,520,786. Such mediators include compounds selected from the group of substituted or unsubstituted 3-phenylimino-3H-phenothiazines and 3-phenylimino-3H-phenoxazines. Appropriate indicators include, without limitation, WST-4, as well as the general classes of 2-thiazolyl tetrazolium salt compounds disclosed in U.S. Pat. Nos. 5,126,275 and 5,322,680. Each of the foregoing patents is assigned to the present assignee and is incorporated herein by reference in its entirety.

In the course of this work, it has been found that the mediators reported in U.S. Pat. No. 5,520,786 as being useful in an electrode-based NAD dependent GDH system can also be used in an optically-based NAD dependent GDH system as described immediately above, as well as an optically based PQQ-GDH reductive system. This result is surprising for at least two reasons. First, mediators can be specific for different enzymes. Not all mediators that work in NAD-GDH systems necessarily work as well in PQQ-GDH systems. Second, the mediators disclosed in U.S. Pat. No. 5,520,786 are colored. While this is not problematic in an electrode-based system such as disclosed in U.S. Pat. No. 5,520,786, one would expect that these mediators could not be used in an optically based system such as disclosed herein. Applicant has found, however, that because these mediators change from colored to colorless during the course of the reaction, they do not interfere with the measurement at the final endpoint. One skilled in the art could envision that though it is generally preferred to measure color generation, color disappearance could also be measured, although the former typically gives better test precision. Thus it is within the scope of this invention to use a PQQ-GDH reductive system with a mediator as disclosed in U.S. Pat. No. 5,520,786, and with the additional one or more polymers to control opacity as disclosed herein. Suitable indicators for such systems include a tetrazolium indicator such as WST-4, available from Dojindo Laboratories, or a tetrazolium salt indicator such as those disclosed in U.S. Pat. Nos. 5,126,275 and 5,322,680 as discussed above.

Porous membrane materials suitable for use in the method of the instant invention include commercially available materials such as porous polyethersulfone membranes such as those sold under the brand name Supor and Presense and available from Pall Corporation; and modified porous polyethersulfone membranes such as those sold under the brand name Predator and available from Pall Corporation. Those skilled in the art will recognize that other porous membranes will be suited to use as membranes in test strips of the instant invention.

Materials suitable for use as the polymer applied to the membrane include, for example, acrylic latex polymers such as those sold under the brand name UCAR and available from Union Carbide, polystyrene sodium sulfate polymers such as those available from Polysciences, Inc., and combinations thereof.

EXAMPLE 1

The dose responses to glucose in both aqueous solution and whole blood for test strips prepared in accordance with the instant invention were determined for both small-pore and large-pore test strip membranes. The porous membranes used were Supor brand polyethersulfone membranes purchased from Pall Corporation, and having isotropic pore sizes of 0.2 microns and 5.0 microns. Each porous membrane was treated with reagent by dipping the smooth reaction side of the membrane in the composition set forth in Table 1.

TABLE 1

| Reagent | Final conc. |
| --- | --- |
| 0.4M Sodium HEPES | 0.2 M |
| WST-4 | 40 mM |
| 40% PSSA, mw = 70 k | 5% |
| UCAR 455 (45% solids) | 10.00% |
| NAD | 10 mM |
| Diaphorase | 1016 U/mL |
| GDH (glucose dehydrogenase) | 1900 U/mL |
| Mutarotase | 3370 U/mL |
| Adjust pH to 7.3-7.5 with NaOH | — |

Figure 2:
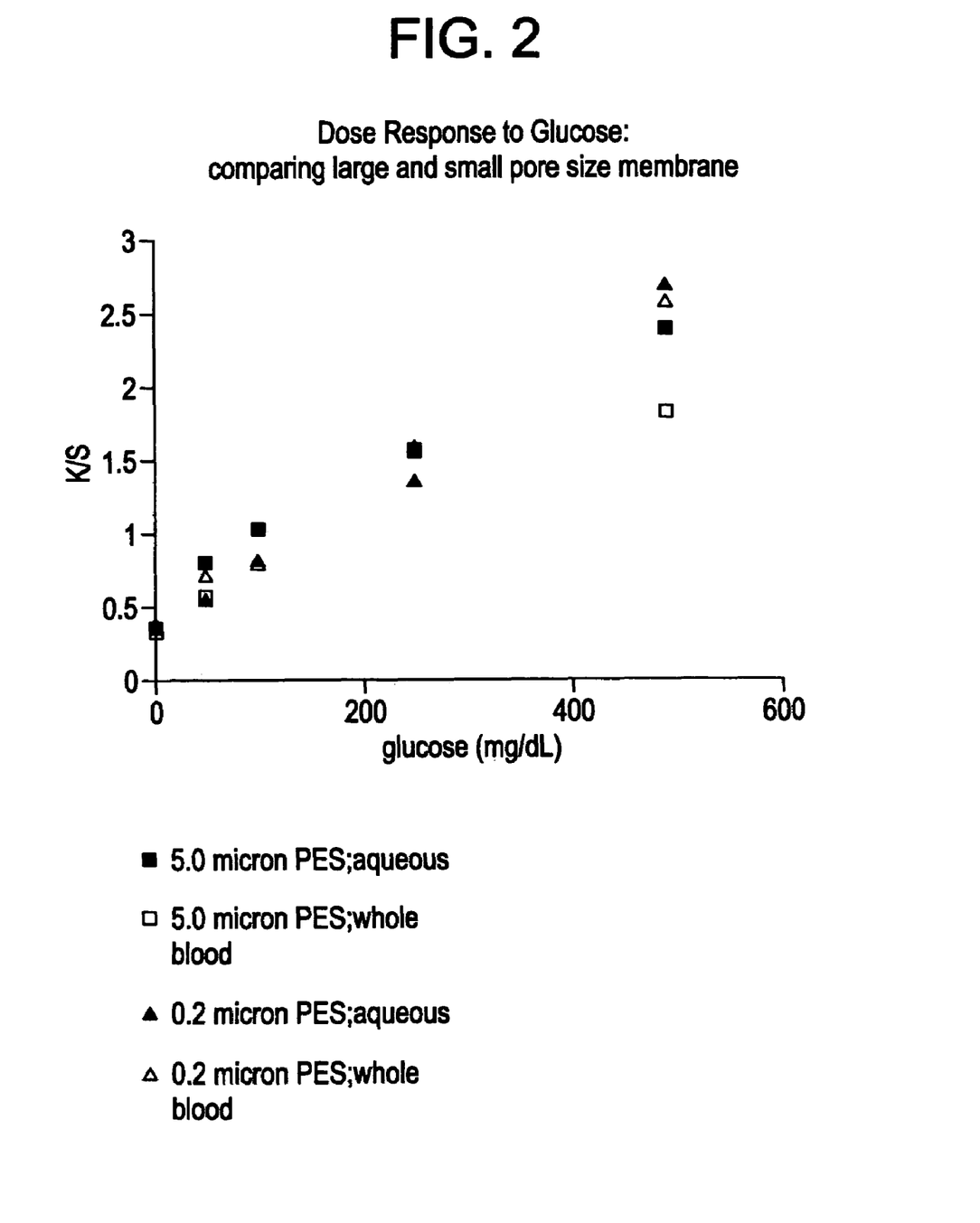
FIG. 2 is a graph of the results achieved with large and small pore size membranes in the detection of glucose in both aqueous solutions and whole blood using test strips prepared in accordance with the invention.

The membranes were dried at 40-50° C. for at least 5 minutes in a high air flow oven. The membranes were cut into discs and fitted into strips as described above in connection with the embodiment of FIG. 1B. A clear polyester film window was applied to the coated reaction side using Arcare 7843 pressure sensitive adhesive available from Adhesives Research. The test strips were oriented with the reaction side facing down. Test samples of 500 nanoliters of either aqueous glucose solution or whole blood spiked with glucose were then applied to the rough sample side of each disc in the test strip. The glucose solutions were buffered to pH 7.5 using 0.15M Na HEPES. The glucose concentrations in the aqueous and whole blood samples were at 0 mg/dL, 50 mg/dL, 100 mg/dL, 250 mg/dL, and 600 mg/dL. The whole blood samples were spiked to the indicated level and measured as plasma glucose using a Yellow Springs Co., Inc. model 2300 STAT Plus glucose detector. Two replicates were run of each sample solution on each sample test strip. The reflectance of each test strip at 680 nm was measured at the clear polyester film window using the apparatus described in co-pending patent application Ser. No. 60/373,583, filed Apr. 19, 2002. This instrument uses a small-read-area reflectance read head of about 0.030 inches diameter. The measured reflectance values R were converted to a linearizing function K/S by the formula $K/S=(1-R)^2/2R$. As shown in FIG. 2, the measured reflectance for each level of glucose was substantially the same for both aqueous solutions and for whole blood, and for the different pore sizes of the test discs, indicating that for test strips made in accordance with the invention the dose response was substantially independent of both membrane pore size and whether or not whole blood was present in the sample.

EXAMPLE 2

This example demonstrates the feasibility of the dipped reagent membrane technique when the samples are applied using a lateral flow, capillary format as illustrated and discussed in connection with FIG. 1C, rather than the flow through technique used in Example 1 above. Samples of 0.8 micron pore size polyethersulfone membrane sold under the trade name "Presense" from Pall Corporation were treated as described in Example 1. Ribbons of the treated membrane were mounted on capillary flow test strips as illustrated in FIG. 1C. Each test strip had applied to it a 600-800 nanoliter sample of either aqueous glucose solution or glucose in 40% hematocrit whole blood. The concentrations of glucose in the aqueous test samples were 0, 50, 100, 250, and 500 mg/dL. The concentrations of glucose in the whole blood samples were 0, 50, 100, 200, 400 and 600 mg/dL, converted to plasma values.

Figure 3:
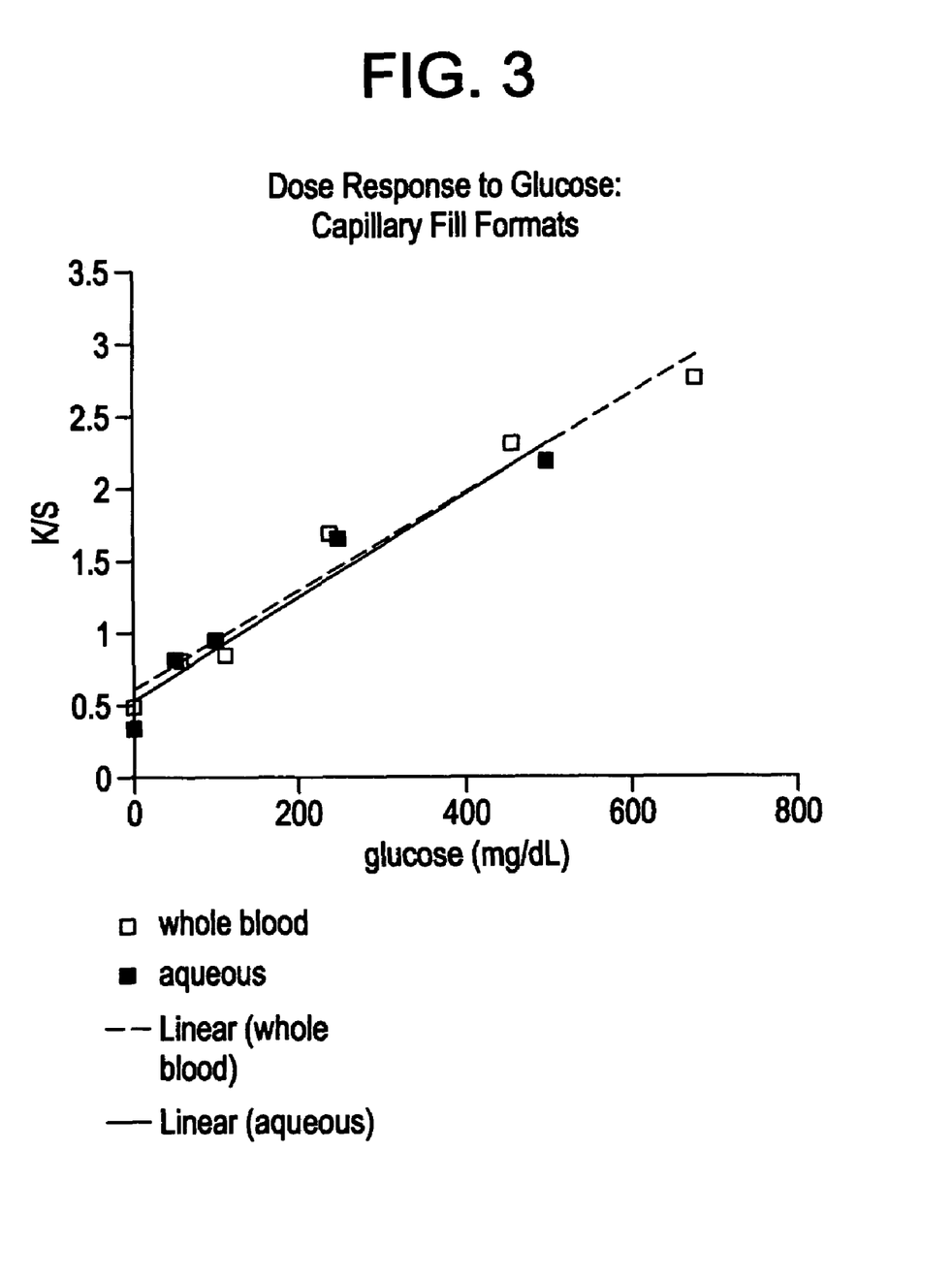
FIG. 3 is a graph showing the response of capillary fill format test strips in accordance with the instant invention for different concentrations of glucose in both aqueous solution and whole blood.

Reflectance was measured at 680 nm at a 30-second endpoint using the instrument described in Example 1, and the values were linearized as described above. The results are illustrated in FIG. 3. It may be seen that the results obtained for the corresponding aqueous and whole blood samples each produced linear functions having substantially the same slope and intercept, indicating that the reflectance values obtained with the test strips of the instant invention were independent of the hematocrit of the whole blood samples.

EXAMPLE 3

Test strips were prepared using 0.8 micron pore size polyethersulfone porous membrane materials sold under the brand name Presense by Pall Corporation. The reagent composition used was that described in Table 1. The reagent composition was applied by striping onto the reaction side of the porous membrane rather than by dipping. The test strips were then provided with clear polyester windows secured by Arcare 7843 pressure-sensitive adhesive, and were laminated with ribbons of reagent, all as described in Example 1 above. The test strips were oriented with the reaction side facing down. Test samples of 500 nanoliters of whole blood spiked with glucose were then applied to the rough sample side of each test strip. The glucose whole blood samples were at 0 mg/dL, 50 mg/dL, 100 mg/dL 200 mg/dL, 400 mg/dL, and 600 mg/dL measured as plasma glucose using a Yellow Springs Instrument detector. Two replicates were run of each sample solution on each sample test strip.

Figure 4:
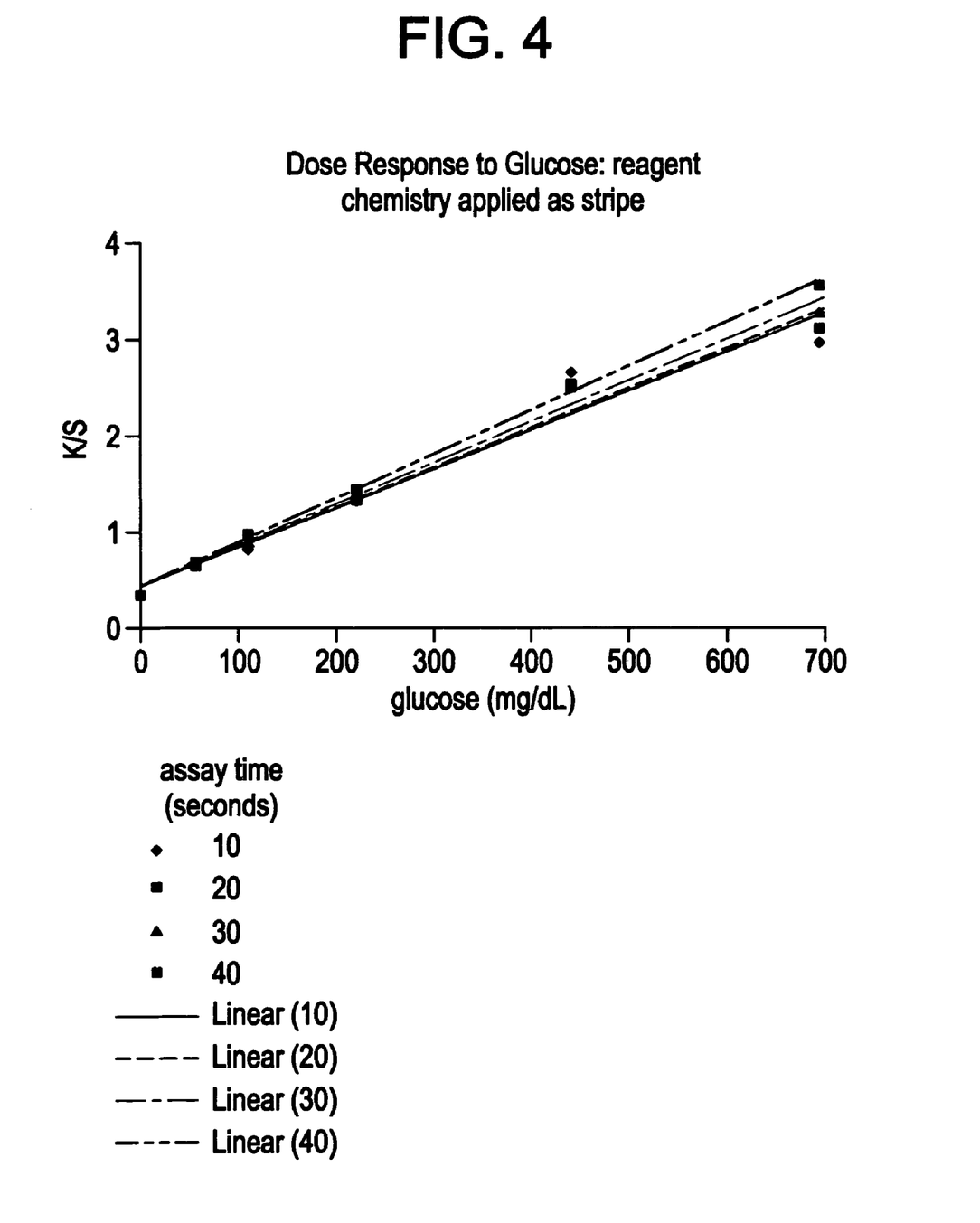
FIG. 4 is a graph showing the response at different endpoints of test strips made in accordance with the invention in which the reactive chemistry is applied to the test strip as a stripe.

The reflectance of each test strip was measured using the instrument described in Example 1 above at 680 nm using a small-read-area reflectance read head of about 0.030 inches diameter. The measured reflectance values R were converted to a linearizing function K/S by the formula $K/S=(1-R)^2/2R$. Reflectance measurements were taken at 10, 20, 30 and 40 seconds. The results are illustrated in FIG. 4. It may be seen that the measured reflectance was proportionate to the glucose dose for the whole blood samples and a rapid and stable endpoint was achieved over the full glucose range, indicating that striping can produce an effective test strip in accordance with the invention.

EXAMPLE 4

This example demonstrates the utility of the mediators reported in U.S. Pat. No. 5,520,786 in an optically based PQQ-GDH reductive system. Reagent was prepared as follows:

TABLE 2

| Reagent | Final conc. |
|---|---|
| 0.4M Sodium HEPES | 0.2 M |
| WST-4 | 40 mM |
| 40% PSSA, mw = 70 k | 5% |
| UCAR 455 (45% solids) | 10.00% |
| PQQ-GDH | 1245 U/mL |
| 3-(3,5-dicarboxyphenylimino)-3H-phenothiazine | 6 mM |
| Adjust pH to 7.3-7.5 with NaOH | — |

Approximately 1 microliter aliquots of the reagent mixture were placed onto pre-cut strips of 0.8 micron polyethersulfone Presence membrane and 0.2 and 5.0 micron polyethersulfone Supor membranes. After air drying at room temperature, 500 nL aliquots of 0, 50, 200 mg/dL aqueous glucose samples were added. Changes in color, the uniformity of color, and the speed of color changes were observed. Visual dose responses were observed for the glucose samples. Aliquots of a similar formulation with 0.1% Silwet L-7600 surfactant and final formulation pH of approximately 7.0 were also placed in a micro-cuvette (e.g. small volume, 50 micron path length) and a dose response with the addition of 0 to 500 mg/dL whole blood glucose was observed. A range of approximately 25 to 5 percent reflectance was observed. These results indicate that 3-(3,5-dicarboxyphenylimino)-3H-phenothiazine can be an effective mediator for the PQQ-GDH determination of glucose in both aqueous and whole blood samples.

EXAMPLE 5

This example demonstrates the feasibility of using a tetrazolium salt indicator such as those disclosed in U.S. Pat. Nos. 5,126,275 and 5,322,680 in a NAD dependent system in the context of this invention. Reagent was prepared as described in Table 1 of Example 1 above except that 40 mM of 2-(4-difluoromethyl-5-chlorothiazol-2-yl)-3-[2-(3-trimethylammonioproproxy)phenyl]-5-(3,4-methylenedioxyphenyl)tetrazolium dimethylsulfonate tetrazolium salt indicator was substituted for the WST-4 tetrazolium salt. The reagent mix was used to coat the smooth side of 0.8 micron polyethersulfone Presence membrane and then assembled into capillary fill formats. A dose response to 0 to 600 mg/dL whole blood glucose was demonstrated with a range of approximately 30 to 10 percent reflectance.

It will be appreciated that the inventive method and test strips disclosed herein offer significant advantages over prior art glucose determination systems. Such prior art glucose determination systems typically require optical readings of a sample at two different wavelengths to correct for the interference introduced by the red blood cells (hematocrit) in the sample. The test strips provide results that are independent of the pore size of the membrane, and substantially independent of the hematocrit of the sample. Since the system is substantially independent of hematocrit, there is no need to measure reflectance at two different wavelengths and apply a correction factor. This means that the optical measurement device used with the system of the instant invention can be much simpler and less expensive than prior art systems, because it will require only one set of optics instead of two. A system used in connection with the instant invention also will not require a complicated algorithm to adjust for the hematocrit or chromatography. The invention also eliminates the need for scattering centers used in prior art systems to adjust for the opacity of a reflective surface. Also, because the sample does not need to undergo any procedure to separate the red blood cells, a much smaller sample size can be used, typically on the order of about 1 microliter or less. The present invention has been described and exemplified above. Those skilled in the art will recognize that other modifications and variations of the invention can be made without departing form the spirit and scope hereof.

What is claimed is:

1. A method for determining analyte concentration in a fluid sample, the method comprising the acts of:

(a) providing a test strip having a sample side and a reaction side, the test strip including a porous membrane, the test strip being adapted to accept a sample on the sample side and pass it towards the reaction side, said test strip including a testing reagent, said testing reagent comprising a color indicator system that changes color to indicate the presence of the analyte in the sample, said test strip further having a polymer on at least the reaction side, said polymer increasing the opacity of at least a portion of the test strip after contact with a sample, said polymer being selected from the group consisting of acrylic latex polymers, polystyrene sodium sulfate polymers, and combinations thereof;

(b) applying the sample to the sample side of the test strip; and (c) measuring the change in color of the testing side to determine the analyte concentration of the sample.

2. The method of claim 1 wherein the analyte is glucose.

3. The method of claim 1 wherein said porous membrane includes polyethersulfones, modified polyethersulfones, or combinations thereof.

4. The method of claim 1 wherein the testing reagent comprises a chemistry system selected from the group consisting of a PQQ-GDH system, a NAD-dependent GDH system, a hexokinase reductive system, and a glucose oxidase oxidative system.

5. The method of claim 1 wherein the indicator system includes tetrazolium compounds or tetrazolium salt compounds.

6. The method of claim 5 wherein the indicator system comprises a 2-thiazolyl tetrazolium salt compound.

7. The method of claim 1 wherein the reagent comprises a mediator compound including a substituted or unsubstituted 3-phenylimino-3H-phenothiazine or 3-phenylimino-3H-phenoxazine.

8. The method of claim 1 wherein said test strip has pore sizes in the range of about 0.2 microns to about 5 microns.

9. The method of claim 8 wherein said test strip is isotropic.

10. The method of claim 8 wherein said test strip is anisotropic.

11. A test strip for measuring an analyte concentration in a fluid sample, the test strip comprising:

(a) a porous membrane having a sample side and a reaction side, the membrane being adapted to accept the sample on the sample side and pass it towards the reaction side;

(b) a testing reagent supported by the membrane, said testing reagent comprising a color indicator system that changes color to indicate the presence of analyte in the sample; and (c) a polymer on at least a portion of the reaction side of the porous membrane, said polymer increasing the opacity of at least a portion of the test strip after contact with the sample, said polymer being selected from the group consisting of acrylic latex polymers, polystyrene sodium sulfate polymers, and combinations thereof.

12. The test strip of claim 11 wherein the analyte is glucose.

13. The test strip of claim 11 wherein said porous membrane includes polyethersulfones, modified polyethersulfones, or combinations thereof.

14. The test strip of claim 11 wherein the testing reagent comprises a chemistry system selected from the group consisting of a PQQ-GDH system, a NAD-dependent GDH system, a hexokinase reductive system, and a glucose oxidase oxidative system.

15. The test strip of claim 11 wherein the indicator system includes tetrazolium compounds or tetrazolium salt compounds.

16. The test strip of claim 15 wherein the indicator system comprises a 2-thiazolyl tetrazolium salt compound.

17. The test strip of claim 11 wherein the reagent comprises a mediator including a substituted or unsubstituted 3-phenylimino-3H-phenothiazine or 3-phenylimino-3H-phenoxazine.

18. The test strip of claim 11 wherein said test strip has pore sizes in the range of about 0.2 microns to about 5 microns.

19. The test strip of claim 18 wherein said test strip is isotropic.

20. The test strip of claim 18 wherein said test strip is anisotropic.

21. The test strip of claim 18 wherein said testing reagent includes a glucose dehydrogenase (GDH) system.

22. The method of claim 1 wherein said testing reagent includes a glucose dehydrogenase (GDH) system.

* * * * *